(12) United States Patent
Kim et al.

(10) Patent No.: US 9,937,324 B2
(45) Date of Patent: Apr. 10, 2018

(54) VARIABLY FLEXIBLE PIPE AND MANIPULATOR

(71) Applicants: Samsung Electronics Co., Ltd., Suwon-si, Gyeonggi-do (KR); Massachusetts Institute of Technology, Cambridge, MA (US)

(72) Inventors: Yong Jae Kim, Seoul (KR); Shan Bao Cheng, Cambridge, MA (US); Sang Bae Kim, Cambridge, MA (US); Karl Iagnemma, Cambridge, MA (US)

(73) Assignees: Samsung Electronics Co., Ltd., Gyeonggi-do (KR); Massachusetts Institute of Technology, Cambridge, MA (US)

( * ) Notice: Subject to any disclaimer, the term of this patent is extended or adjusted under 35 U.S.C. 154(b) by 321 days.

(21) Appl. No.: 13/853,267

(22) Filed: Mar. 29, 2013

(65) Prior Publication Data

US 2013/0289478 A1 Oct. 31, 2013

(30) Foreign Application Priority Data

Mar. 30, 2012 (KR) ........................ 10-2012-0033479

(51) Int. Cl.
*A61F 11/00* (2006.01)
*A61M 25/01* (2006.01)
(Continued)

(52) U.S. Cl.
CPC ..... *A61M 25/0147* (2013.01); *A61B 1/00078* (2013.01); *A61M 25/0043* (2013.01);
(Continued)

(58) Field of Classification Search
CPC . A61B 1/00078; A61B 1/0051–1/0053; A61B 1/0055; A61B 1/0057;
(Continued)

(56) References Cited

U.S. PATENT DOCUMENTS 3,998,216 A * 12/1976 Hosono ................ A61B 1/0055
600/140
4,815,450 A    3/1989 Patel
(Continued)

FOREIGN PATENT DOCUMENTS

DE         19729499      * 1/1999
JP     2010-534529 A     11/2010
(Continued)

OTHER PUBLICATIONS

Circular. (n.d.) American Heritage Dictionary of the English Language, Fifth Edition. (2011). Retrieved Apr. 8, 2016 from http://www.thefreedictionary.com/circular.*

(Continued)

*Primary Examiner* — Katrina Stransky
*Assistant Examiner* — Kankindi Rwego
(74) *Attorney, Agent, or Firm* — Harness, Dickey & Pierce, P.L.C.

(57) ABSTRACT

Disclosed herein is a variably flexible pipe including at least one flap member having variable flexibility and a tube formed of an elastically deformable material and accommodating the at least one flap member, and a manipulator having the same. The at least one flap member may include a plurality flap parts and a connection part to which one side of each of the plurality of flap parts is connected, and the tube changes pressure applied to the plurality of flap parts according to a controlled change of the inner pressure of the tube, thereby causing the variably flexible pipe to be effectively selectively maintained in a deformed state.

17 Claims, 10 Drawing Sheets

(51) Int. Cl.
*A61B 1/00* (2006.01)
*A61M 25/00* (2006.01)
*F16L 11/12* (2006.01)
*A61B 1/005* (2006.01)

(52) U.S. Cl.
CPC ............. *F16L 11/12* (2013.01); *A61B 1/0055* (2013.01); *A61M 25/0155* (2013.01); *A61M 2025/0063* (2013.01)

(58) Field of Classification Search
CPC ..... A61B 1/0154; A61B 1/005; A61B 1/0056; A61B 1/0058; A61B 1/008; A61B 1/01; A61B 1/012; A61B 1/0125; A61B 1/015; A61B 1/018; A61B 2017/00305; A61B 2017/00314; A61M 2025/0063; A61M 25/0043; A61M 25/0147; A61M 25/0155
USPC .................................. 600/139, 144; 606/108
See application file for complete search history.

(56) References Cited

U.S. PATENT DOCUMENTS

| | | | | |
|---|---|---|---|---|
| 4,834,069 | A * | 5/1989 | Umeda | A61B 1/0055 138/120 |
| 5,271,382 | A * | 12/1993 | Chikama | A61B 1/0055 138/120 |
| 6,942,613 | B2 * | 9/2005 | Ewers | A61B 1/0008 600/114 |
| 7,598,651 | B2 * | 10/2009 | Kornbluh | B64C 3/48 310/309 |
| 2003/0032859 | A1 | 2/2003 | Belson | |
| 2008/0021277 | A1 | 1/2008 | Stefanchik et al. | |
| 2009/0030282 | A1 * | 1/2009 | Garcia | B25J 18/06 600/146 |
| 2009/0143642 | A1 | 6/2009 | Takahashi et al. | |
| 2010/0010309 | A1 * | 1/2010 | Kitagawa | A61B 1/0052 600/142 |

FOREIGN PATENT DOCUMENTS

| | | |
|---|---|---|
| JP | 2011-067423 A | 4/2011 |
| JP | 2011-194126 A | 10/2011 |
| KR | 10-2008-0111925 | 12/2008 |
| KR | 10-2010-0138489 | 12/2010 |

OTHER PUBLICATIONS

EPO Machine Translation of DE 19729499. Retrieved Apr. 8, 2016 from http://worldwide.espacenet.com.*
Yong-Jae Kim et al., "Design of a Tubular Snake-like Manipulator with Stiffening Capability by Layer Jamming", 2012 IEEE/RSJ International Conference on Intelligent Robots and Systems, Oct. 7-12, 2012, pp. 4251-4256.
Arjo Loeve et al, "Scopes Too Flexible . . . and Too Stiff", IEEE Pulse, Nov./Dec. 2010, vol. 1, No. 3, pp. 26-41.
European Search Report dated Feb. 13, 2014 in related European Application No. 13161961.1.
Office Action for corresponding European Patent Office application No. 13 161 961.1 dated Oct. 8, 2015.
Notification of Granting of Patent Right to Invention dated Aug. 1, 2016 in Chinese Application No. 201310102192.2.
European Office Action dated Jul. 7, 2016 in Application No. 13 161 961.1-1666.
Japanese Office Action dated Nov. 21, 2016 for corresponding JP Application No. 2013-070199.
Summons to attend oral proceedings pursuant to Rule 115(1) EPC issued by the European Patent Office dated Mar. 22, 2017 for EP Application No. 13161961.1.
Decision of Patent dated Mar. 14, 2017 for Japanese Patent Application No. 2013-070199.
European Patent Office Communication for EP Application No. 13 161 961.1.

* cited by examiner

VARIABLY FLEXIBLE PIPE AND MANIPULATOR

CROSS-REFERENCE TO RELATED APPLICATIONS

This application claims the benefit of Korean Patent Application No. 2012-0033479, filed on Mar. 30, 2012 in the Korean Intellectual Property Office, the disclosure of which is incorporated herein by reference.

BACKGROUND

1. Field

One or more embodiments relate to a variably flexible pipe and manipulator, and more particularly, one or more embodiments relate to a selectively changed flexibility of such a variably flexible pipe and manipulator for the same.

2. Description of the Related Art

A manipulator may be a device that can be used for minimally invasive surgery procedures, for example, and may include a flexible pipe that may be inserted into one or more cavities of a body and/or inserted toward a particular position within the body, such as through one or more surgically created openings in a human body.

As only an example, this flexible pipe may be flexibly deformed, such as by a surgeon that is controlling the manipulator, during the process where the flexible pipe is inserted into the one or more cavities and/or toward the particular position, and typically requires controlling the wires of the flexible pipe to maintain a final deformation or flexing upon the flexible pipe reaching a surgical site within the body. Then a surgical instrument may be inserted into the body, e.g., through the flexible pipe, and then manipulated at the surgical sight from outside the body.

SUMMARY

Therefore, one or more embodiments provide a variably flexible pipe, flexibility of which is selectively changed, and a manipulator having the same.

One or more embodiments include a variably flexible pipe including a longitudinal pipe structure, with a hollow interior, configured to have variable flexibility, the variable flexibility being created by plural components of the longitudinal structure that are configured to move relative to each other differently according to at least a first state and second state, the first state being where the plural components move relative to each other dependent on a first friction generated by the variably flexible pipe between the plural components, and the second state being where the plural components move relative to each other based on a second friction generated by the variably flexible pipe between the plural components, with the first friction being less than the second friction, and a tube that may be formed of a deformable material configured to cover the plural components and to control the longitudinal structure to selectively be in one of the first state and the second state based on a difference between a controllable pressure inside the tube and a pressure outside of the tube.

One or more embodiments include a manipulator including a variably flexible pipe, flexibility of which is selectively changed, a plurality of wires configured to pas through the variably flexible pipe and connected to a front end of the variably flexible pipe, and a plurality of actuators respectively configured to apply force to the plurality of wires so as to bend the variably flexible pipe, wherein the variably flexible pipe may include a longitudinal pipe structure, with a hollow interior, configured to have variable flexibility, the variable flexibility being created by plural components of the longitudinal structure that are configured to move relative to each other differently according to at least a first state and second state, the first state being where the plural components move relative to each other dependent on a first friction generated by the variably flexible pipe between the plural components, and the second state being where the plural components move relative to each other based on a second friction generated by the variably flexible pipe between the plural components, with the first friction being less than the second friction, and a tube that may be formed of a deformable material configured to cover the plural components and to control the longitudinal structure to selectively be in one of the first state and the second state based on a difference between a controllable pressure inside the tube and a pressure outside of the tube.

The manipulator may further include a pneumatic pump controlling a change in the pressure inside the tube to control the longitudinal structure to be in one of the first state and second state.

The longitudinal structure may include at least one flap member having variable flexibility and the plural components may be components of the at least one flap member and include a plurality of flap parts and a connection part to which one side of each of the plurality of flap parts is connected, and the tube may be formed of an elastically deformable material and accommodates the at least one flap member, wherein the longitudinal structure may be controlled to be in the one of the first state and the second state based upon a change in pressure transmitted to the plurality of flap parts according to a controllable change in the pressure inside the tube.

The longitudinal structure may further include a plurality of link members formed in respective ring shapes and sequentially disposed in the longitudinal direction of the longitudinal structure, wherein the at least one flap member may be disposed on circumferentially outer surfaces of the plurality of link members, and the tube may be installed so as to cover the circumferentially outer surface of the at least one flap member and circumferentially inner surfaces of the plurality of link members.

Each of the plurality of link members may a pair of first hinge parts provided at different positions along a first surface of each of the plurality of link members and connected to a link member neighboring the first surface, and a pair of second hinge parts provided at different positions along a second surface, distinguished from the first surface, of each of the plurality of link members and connected to a link member neighboring the second surface.

The pair of first hinge parts and the pair of second hinge parts may be provided at the respectively different positions separated by an angle of 90° in the circumferential direction.

The first hinge parts may include hinge protrusions protruded in a circular shape and rotatably installed in the second hinge parts, and the second hinge parts may include hinge recesses indented in a circular shape so that the hinge protrusions are rotatably installed in the hinge recesses.

The at least one flap member may further include a pair of flap members covering the pair of first hinge parts and the pair of second hinge parts connecting two neighboring link members, and the pair of flap members may further include a first flap member, the plurality of flap parts of which is extended in a first direction and covers the pair of first hinge parts and the pair of second hinge parts, and a second flap member, the plurality of flap parts of which is extended in a second direction different from the first direction and covers the pair of first hinge parts and the pair of second hinge parts.

The at least one flap member includes a plurality of flap members respectively disposed on the outer circumferential surfaces of the plurality of link members in a ring shape.

The least one flap member may be bent in a spiral shape so as to form a tubular shape, and the tube may be formed so as to cover an outer surface and an inner surface of the at least one flap member bent in the spiral shape.

The plurality of flap parts may extend from the connection part of the flap member in one direction.

The plurality of flap parts may extend from the connection part in two directions.

The plurality of flap parts may extend from the connection part so as to have a width that gradually decreases from the connection part.

Additional aspects and/or advantages will be set forth in part in the description which follows and, in part, will be apparent from the description, or may be learned by practice of one or more embodiments of the present invention.

BRIEF DESCRIPTION OF THE DRAWINGS

These and/or other aspects will become apparent and more readily appreciated from the following description of embodiments, taken in conjunction with the accompanying drawings of which.

DETAILED DESCRIPTION

Reference will now be made in detail to one or more embodiments, illustrated in the accompanying drawings, wherein like reference numerals refer to like elements throughout. In this regard, embodiments may be embodied in many different forms and should not be construed as being limited to embodiments set forth herein. Accordingly, embodiments are merely described below, by referring to the figures, to explain aspects of the present invention.

Figure 1:
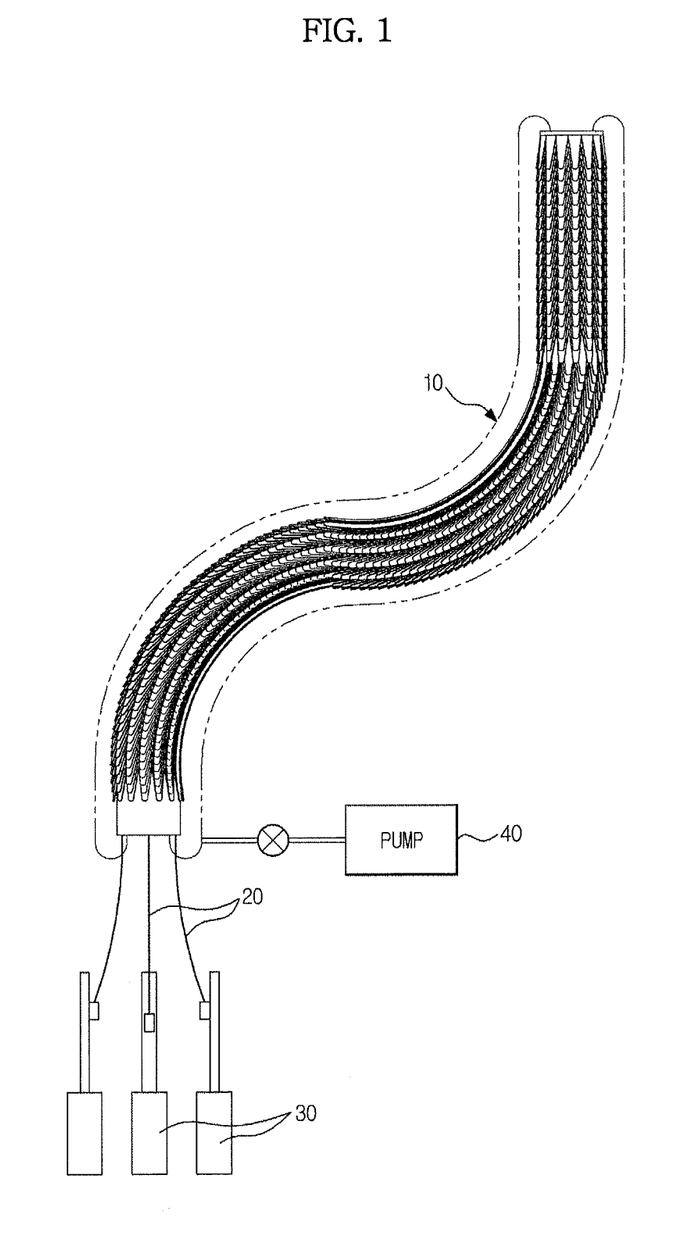
FIG. 1 is a schematic view of a manipulator, according to one or more embodiments.

As shown in FIG. 1, according to one or more embodiments, a manipulator may include one or more variably flexible pipes 10, flexibility of which may be selectively changed. In one or more embodiments, the manipulator may include a plurality of wires 20 that may pass through the variably flexible pipe 10 so that one end of one or more of the plural wires 20 is installed or terminates at a first end, i.e., a front end, of the variably flexible pipe 10, for example. One or more actuators 30 may be respectively connected to the other ends of the plural wires 20 before the plural wires 20 initially enter a second end, i.e., the trailing end, of the variably flexible pipe 10 and may be controlled to control an application of force to the wires 20 so as to selectively deform the variably flexible pipe 10. In one or more embodiments, the manipulator may further include a pneumatic pimp 40 controlling a transmitting of pneumatic pressure to an inside of a tube 14, which will be described in greater detail further below. Although FIG. 1 exemplarily illustrates three wires 20 and three actuators 30, the number of the wires 20 and the number of the actuators 30 are not limited thereto. Similarly, embodiments are not limited to using wires, actuators, and/or pneumatic pumps, but may use components that achieve similar goals for controlling the variably flexible pipe 10, as only an example.

Figure 2:
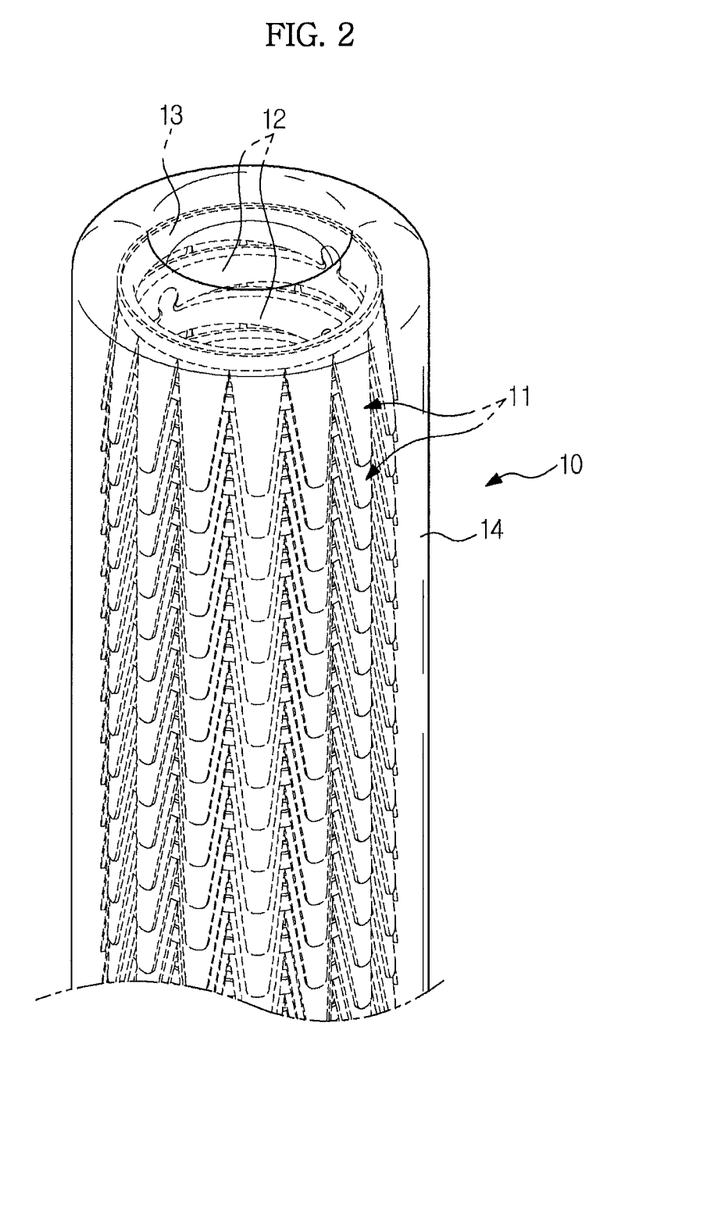
FIG. 2 is a perspective view of a variably flexible pipe, such as applied in the manipulator of FIG. 1, according to one or more embodiments.
Figure 3:
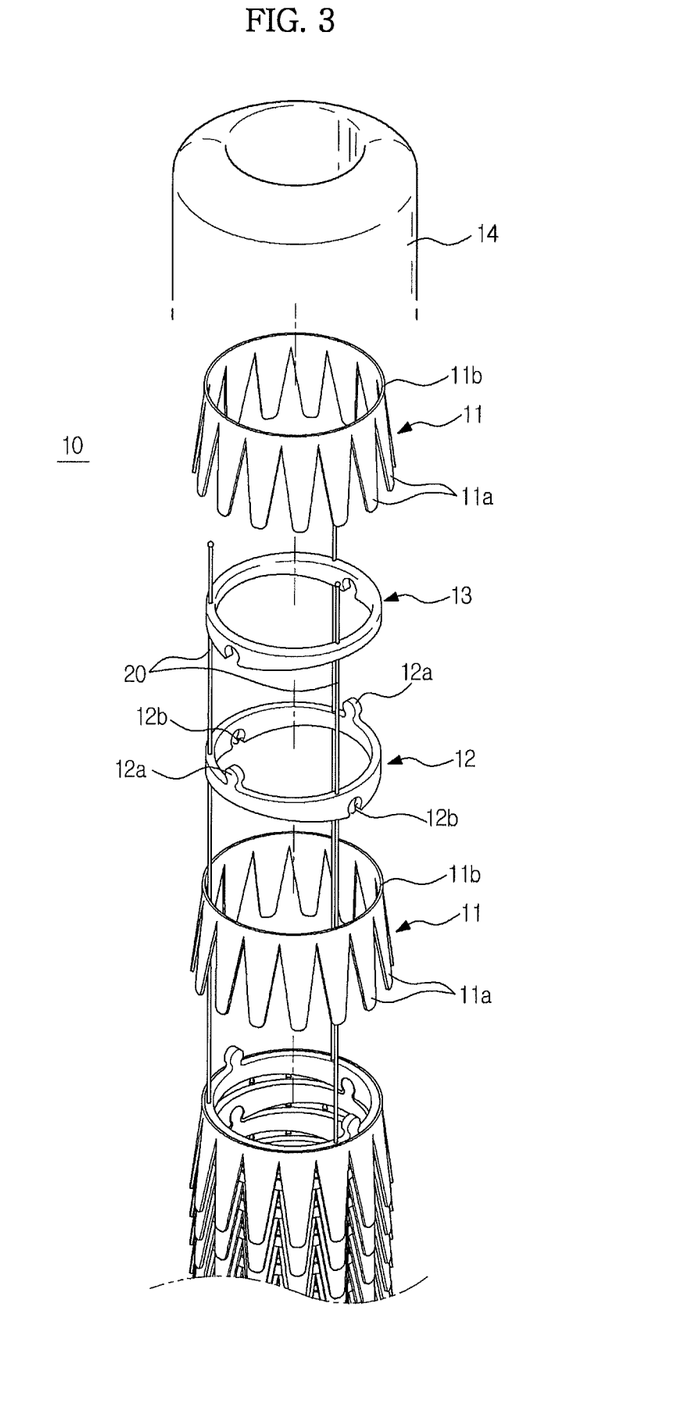
FIG. 3 is an exploded perspective view of a variably flexible pipe, such as applied in the manipulator of FIG. 1, according to one or more embodiments.
Figure 4:
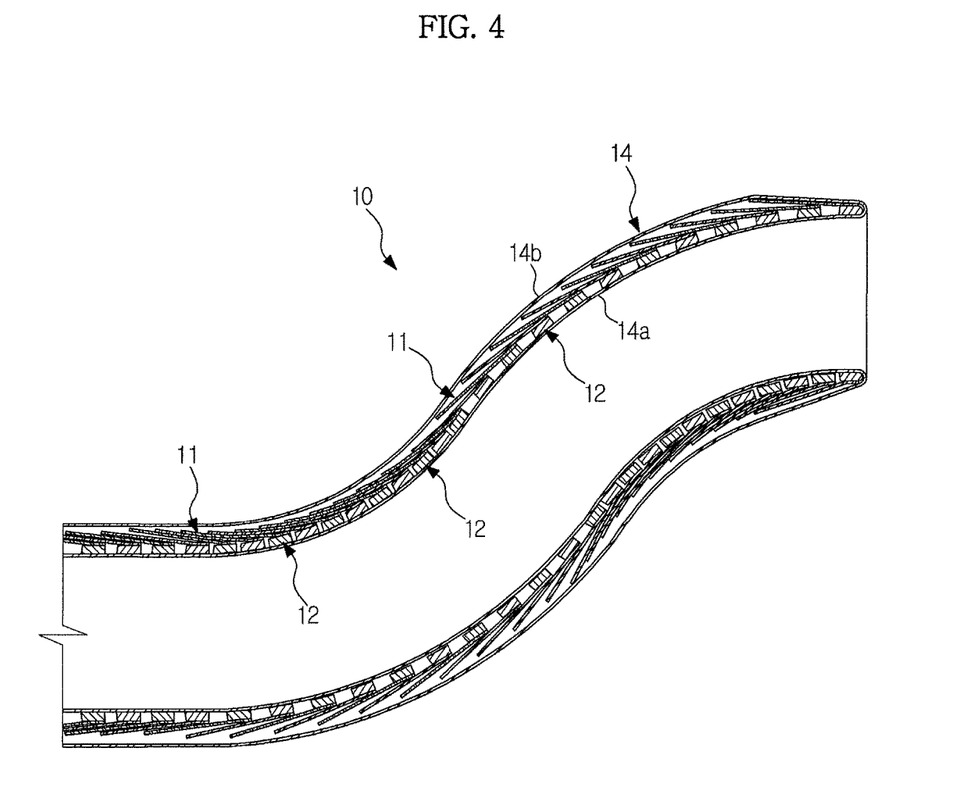
FIG. 4 is a cross-sectional view of a variably flexible pipe, such as applied in the manipulator of FIG. 1, according to one or more embodiments.

In one or more embodiments, the variably flexible pipe 10 may be controlled to be extended or shortened to have a designated length and, as shown in FIGS. 2 to 4 as only respective examples, may include one or more of a plurality of flap members 11, flexibility of which may be selectively controlled, a plurality of link members 12 that may form a ring shape and be sequentially provided in a longitudinal direction of the variably flexible pipe 10, and the tube 14 installed so as to cover the inner surfaces of the link members 12 and/or the outer surfaces of the flap members 11. In one or more embodiments an inner tube pressure of the variably flexible pipe 10, such as within an inner surface of the variably flexible pipe 10, as formed by the tube 14, may be controlled to change, such as by controlling the pneumatic pressure transmitted from the pneumatic pump 40, as only an example. Further, in one or more embodiments an end cap 13 may be connected to a link member 12, e.g., on which the above-described ends of the wires 20 may be installed or terminate, so the end cap 13 may be disposed at the first end of the variably flexible pipe 10.

In one or more embodiments, each of the example flap members 11 may include plural flap parts 11a extended in one direction and a connection part 11b that may be connected to one side of each of the plural flap parts 11a. The connection part 11b may be bent in a ring shape so that the flap member 11 is formed in the ring shape, and may be disposed along an outer circumferential surface of at least the above-described link member 12, as only an example. In an embodiment, the flap parts 11a may be extended in a direction from or toward the second end, i.e., the trailing end, of the variably flexible pipe 10 so that the flap parts 11a have a width that gradually decreases from the connection part 11b. As noted, in one or more embodiments, the plural flap parts 11a and the connection part 11b may be formed along an outer circumference of the link member 12, but embodiments are not limited to the same.

In one or more embodiments, each link member 12 may include a pair of first hinge parts 12a provided at different positions along a first surface of a link member 12 facing the first end of the variably flexible pipe 10 and connected to another link member 12 adjacent to the first surface, and the pair of second hinge parts 12b of the link member 12 may be provided at different positions along a second surface of the link member 12 facing the second end of the variably flexible pipe 10 and connected to another link member 12 adjacent the second surface. In one or more embodiments, plural link members 12 may be stacked with such respective interlocking or connected first hinge parts 12a and second hinge parts 12b of adjacent like members 12. In one or more embodiments, such interlocking or connecting of the first hinge parts 12a and second hinge parts 12b may still provide the capability for adjacent link members 12 to rotate or move relative to each other.

In such an embodiment, and only as a non-limiting example, first hinge parts 12a may be hinge protrusions that protrude from at least one surface of a corresponding link member 12, e.g., each protruding with in a circular shape, as only an example, and second hinge parts 12b on at least another surface of the corresponding link member 12 may be represented by hinge recesses, e.g., indented in such a circular shape, and thus multiple link members 12 may be sequentially installed so as to be rotatable with each other within at least a designated angle, for example. In an embodiment, at least a pair of first hinge parts 12a and at least a pair of second hinge parts 12b provided on respective surfaces of one link member 12 may be provided on each surface and separated on each surface by an angle of 90° in the circumferential direction, as only an example. Although such an embodiment may represent the first hinge parts 12a as hinge protrusions and the second hinge parts 12b as hinge recesses, the first hinge parts 12a and the second hinge parts 12b are not limited thereto, as alternate linking elements between such sequential link members may equally be applied and/or utilized.

In one or more embodiments, the tube 14 may be formed to have a shape, e.g., a donut shaped cross section, such that an outer surface 14a along an inner circumference of the tube 14 produces a longitudinally hollow space, and such that an inner surface 14b along an outer circumference of the tube 14 longitudinally encapsulates the flap members 11 within the tube 14. In one or more embodiments the tube 14 may be a single longitudinal tube, as only an example. In one or more embodiments the tube 14 may be one or more layers of a material or different materials. The link members 12 and the flap members 11 may accordingly be both accommodated in the tube 14, and the tube 14 may formed of a material which is elastically deformable according to the inner pressure thereof, such as latex rubber, as only an example. In one or more embodiments the inner circumference of the tube 14 and/or the outer circumference of the tube 14 may be made of one or more materials that provides sufficient non-reactiveness, durability, strength, and protection for surgical procedures and for an insertion of one or more surgical tools through the tube 14 to perform a surgical act at the surgery site, as only an example. In one or more embodiments, one or more inner pressures of such a tube 14 may be controlled to be changed according to pressure being controlled to be transmitted from the pneumatic pump 40, as only an example, so that a change in pressure is applied to one or more of the flap members 11 provided in the tube 14.

Figure 5:
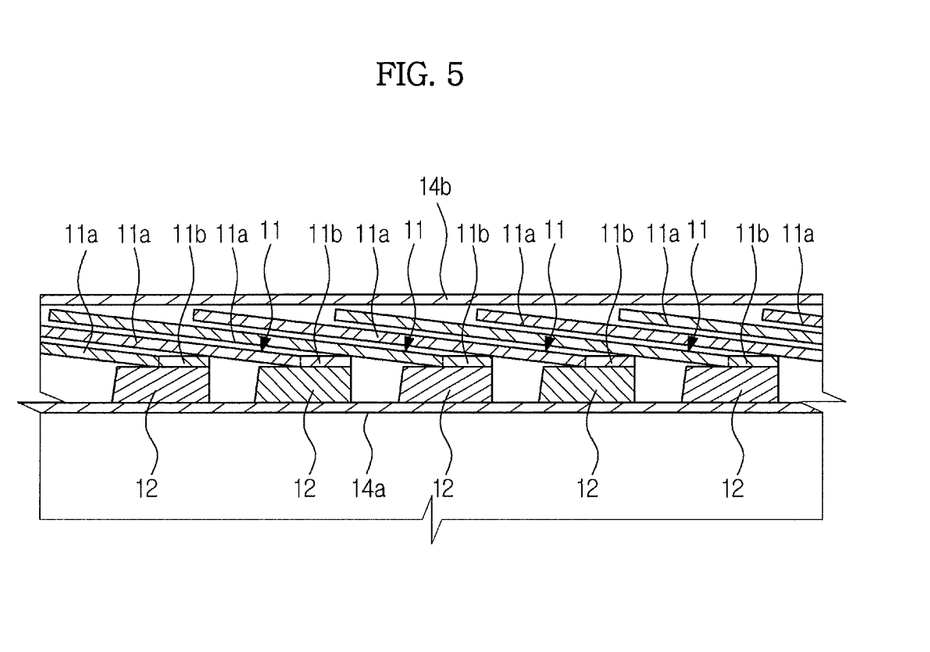
FIGS. 5 and 6 are cross-sectional views illustrating an operation of a variably flexible pipe, such as applied in the manipulator of FIG. 1, according to one or more embodiments.

Initially, a pressure sensitive element may be injected into the tube 14 through the pneumatic pump 40, as only an example, so that an inner pressure of the tube 14 becomes equal to or greater than atmospheric pressure, such as shown in FIG. 5, again as only an example. In one or more embodiments, if the variably flexible pipe is used in an environment where the local environment surrounding the variably flexible pipe is a higher or lower pressure than the referenced atmospheric pressure, then the local higher or lower pressure should be referred to instead of the atmospheric pressure. In one or more embodiments, the pressure sensitive element is a gas, and the gas may further be environmental or filtered air, depending on the environment the variably flexible pipe is expected to be used in. In order to cause frictional force to act between the flap parts 11a, pressure or force needs to be applied to the flap parts 11a. In one or more embodiments, a compression force may selectively be caused to be applied to the flap parts 11a so as to selectively increase the frictional force sufficiently that the flap parts 11a are compressed against one or more of other flap parts 11, link members 12, and/or the connection part 11b. Alternatively, in one or more embodiments, when the inner pressure of the tube 14 is caused to be equal to or greater than an exterior atmospheric pressure, compressing forces that would have been applied to the flap parts 11a, e.g., by the exterior atmospheric pressure against the exterior wall of the tube 14 when there is insufficient spacing between the exterior wall of the tube 14 and the flap parts, may be offset by the inner pressure of the tube 14 being equal or greater than the atmospheric pressure. In such a state, with little or less frictional force being generated between the flap parts 11a of the flap members 11 disposed in the tube 14, even if frictional force is generated between components of the variably flexible pipe, such frictional forces may be selectively controlled to be very low. Accordingly, with little or less frictional force being generated between components of the variably flexible pipe, the flap parts 11a may easily slide along the surfaces of the neighboring flap parts 11a and move relative to each other. Therefore, as only an example, with such little or less frictional force, when the variably flexible pipe 10 is deformed and/or inserted in or through an opening of a body, e.g., by applying longitudinal and/or lateral forces thereto or manipulation of wires 20, the variably flexible pipe 10 may be easily deformed, e.g., by wires 20, to a desired shape and to reach a surgical site. At that point the user may desire, or there may be an automatic determination, that the pressure within the tube 14 should be caused to be decreased, increasing the frictional forces within the components of the variably flexible pipe. In one or more embodiments, the pressure of the tube 14 may be decreased to a particular user desired, acceptable, and/or predetermined level to either substantially minimize or prevent movement between components of the variably flexible pipe, e.g., so the variably flexible pipe maintains the deformed and/or inserted shape while at the surgical site.

Figure 6:
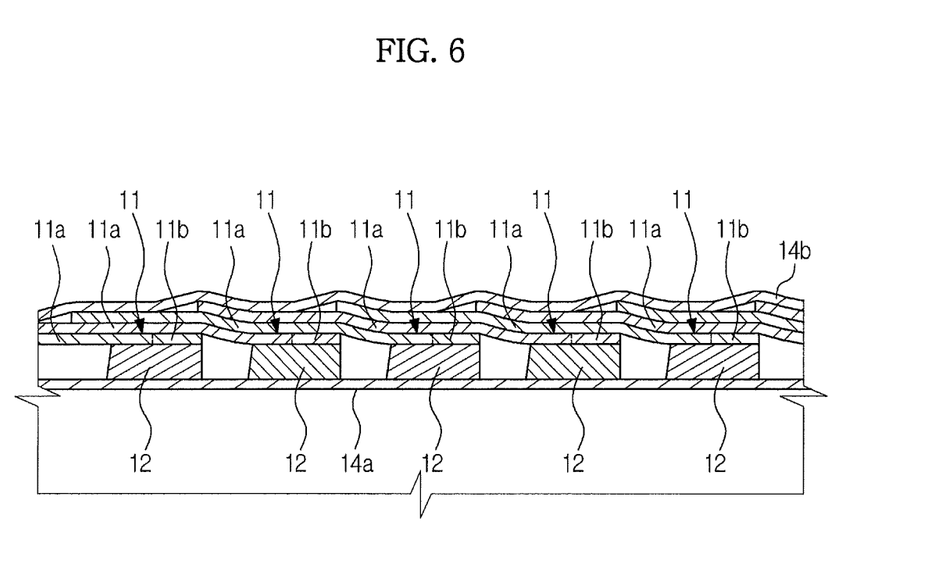

Accordingly, if the first end of the deformed variably flexible pipe 10 reaches a desired position within the body, for example, and a user or an automated decision maker then desires or requires maintenance of the shape of the variably flexible pipe 10, air in the tube 14 may be caused to be removed, e.g., by control of the pneumatic pump 40. For example, the inner pressure of the tube 14 may be decreased to below atmospheric pressure. Then, exterior compressing pressure due to atmospheric pressure acting on the exterior wall of the tube 14, which then acts on the flap members 11, causes the flap parts 11a to be adhered to each other, such as shown in FIG. 6 as only an example. The frictional force may also be increased if the interior pressure of the tube 14 is sufficiently reduced so as to itself apply frictional force to the remaining components of the variably flexible pipe through an inward collapsing of the exterior wall of the tube 14, depending on the material of the tube 14. Accordingly, in one or more embodiments, such increasing or decreasing of frictional force between the flap parts 11a respectively suppresses or permits movement of the neighboring flap parts 11a contacting the flap parts 11a, and thus deformation of the variably flexible pipe 10 is respectively suppressed or permitted. Thus, in one or more embodiments, the suppression of movement may be variably controlled so as to permit more movement, less movement, or no movement.

Said another way, in one or more embodiments, the variably flexible pipe 10 may be controlled to be in a first state in which the variably flexible pipe 10 is easily deformable, a second state in which deformation of the variably flexible pipe 10 is suppressed, or any of one or more different compression force applying states somewhere between the first and second states, according to changes of the inner pressure of the tube 14.

Figure 7:
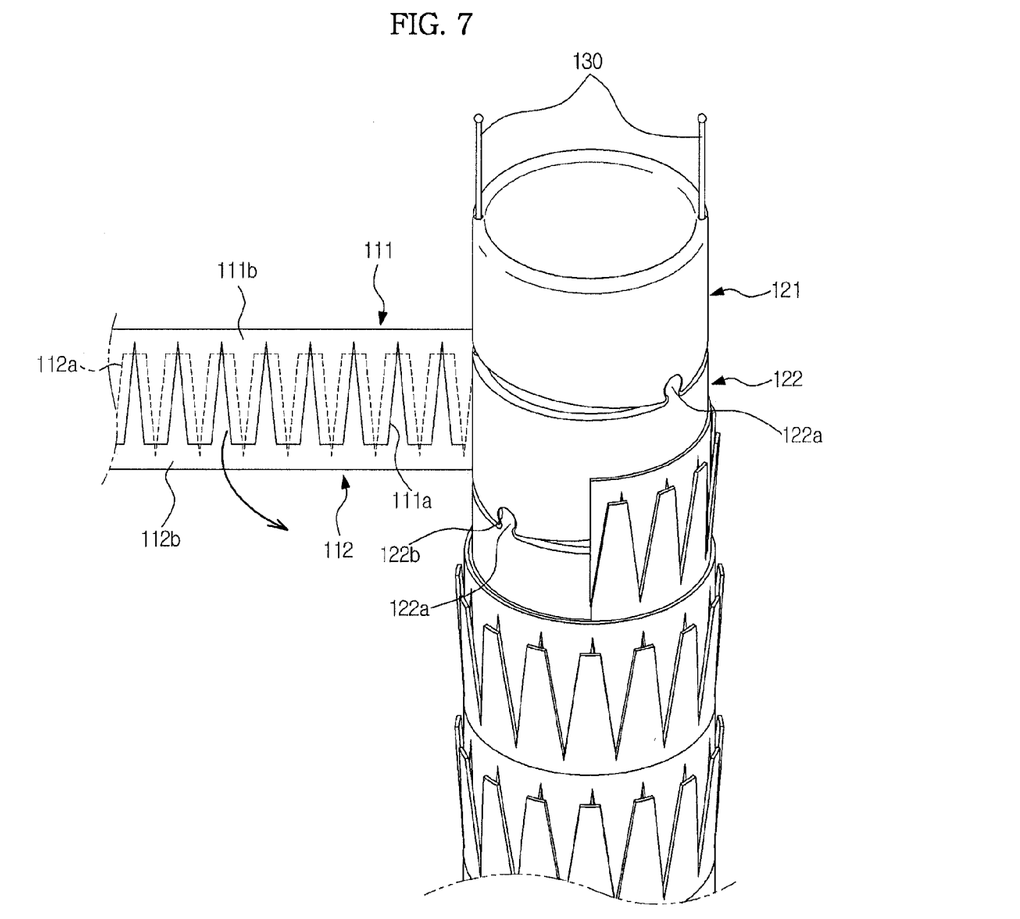
FIG. 7 is an exploded perspective view of a variably flexible pipe applied in a manipulator, according to one or more embodiments.

FIG. 7 is an exploded perspective view of a variably flexible pipe, such as applied in a manipulator, according to one or more embodiments.

As shown in FIG. 7, and only as an example, a variably flexible pipe 10 may include first flap members 111, including applying such first flap members 111 at least onto a first of two neighboring link members 122, and second flap members 112, each including applying such second flap member 112 at least onto a second of the two neighboring link members 122. In one or more embodiments, the first and second neighboring link member 122 may be linked through interlocking portions of each link member 122, without limiting embodiments that include other linking elements that may be applied between each link member 122, e.g., so the first and second flap members 111,112 are respectively applied to the first and second neighboring link members 122 with such other linking members therebetween. Here, such one or more embodiments may include applying the first flap member 111 that includes or caused to include first flap parts 111a extended in a first direction, e.g., applying the first flap parts 111a so they are covering outer circumferential surfaces of example respective first hinge parts 122a and second hinge parts 122b connecting the two neighboring link members 122, and the second flap member 112 that includes or is caused to include second flap parts 112a extended in a second direction, e.g., opposite to the first direction, applying the second flap parts 112a so they are covering outer circumferential surfaces of the first hinge parts 122a and the second hinge parts 122b.

In one or more embodiments, the applying of the first and second flap members may be performed with the first flap member 111 and the second flap member 112 having the same or a greater length than the circumference of the link member 122, and may include applying the first and second flap members 111,112 so they are wound around two link members 122 plural times, as shown in FIG. 7, as only an example. Here, in an embodiment, the length of the first and second flap members 111,112 may be greater than plural circumferences of the link member 122 and the applying of the first and second flap members 111,112 may include applying, e.g., winding, of the first and second flap members 111,112 over multiple neighboring link members. In FIG. 7, in one or more embodiments, the illustrated wires 130 may act similarly to the wires 20 described with regard to FIG. 3. In one or more embodiments the first flap parts 111a and the second flap parts 112a may be applied so as to be alternately disposed in the radial direction on the outer surfaces of the first hinge parts 122a and the second hinge parts 122b, such as shown in FIG. 8 as only an example.

Figure 8:
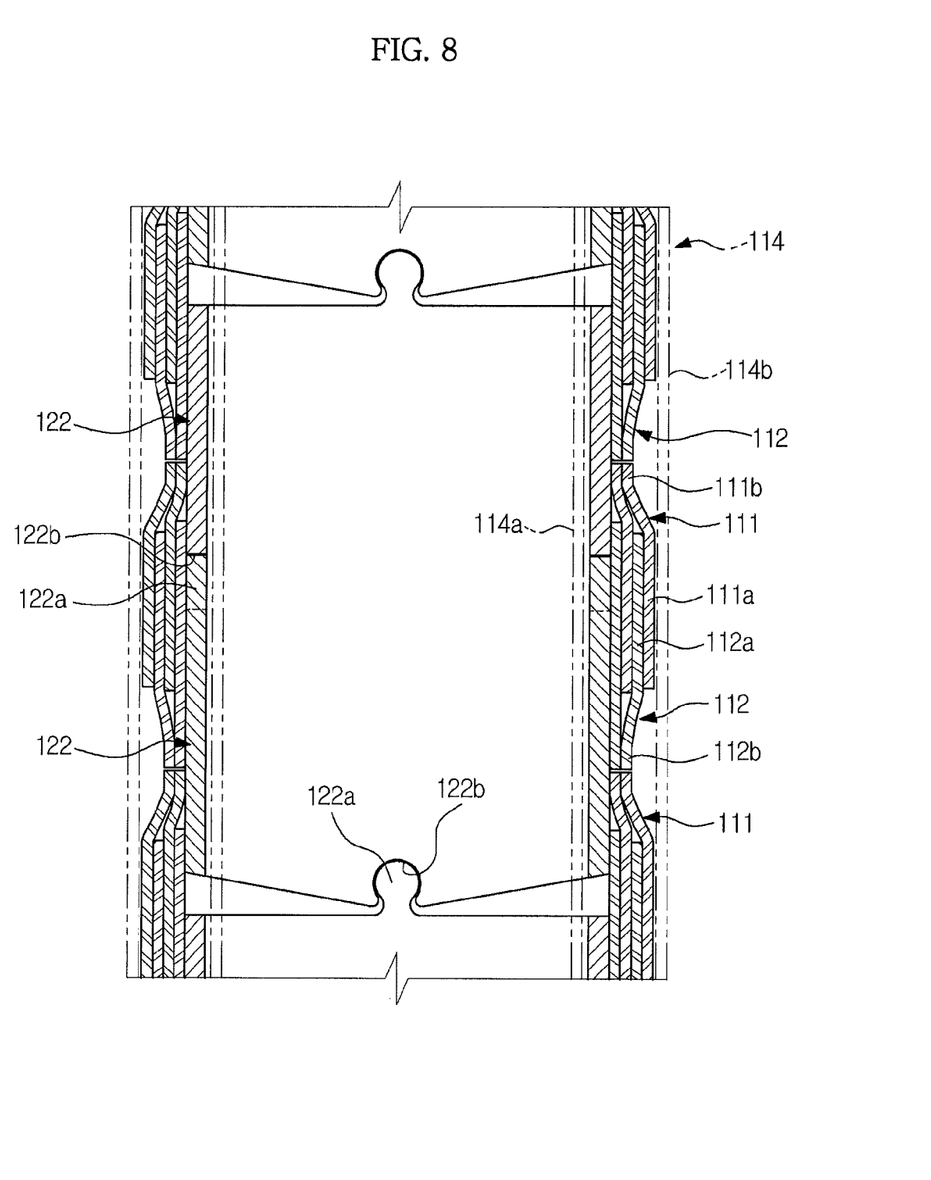
FIG. 8 is a cross-sectional view of a variably flexible pipe, such as applied in a manipulator, according to one or more embodiments.

As illustrated in FIG. 8, a tube 114 accommodates the link members 122, the first flap members 111, the second flap members 112, an inner circumferential surface 114a of the tube 114, and an outer circumferential surface 114b of the tube 114 that covers the first and second flap members 111,112.

Figure 9:
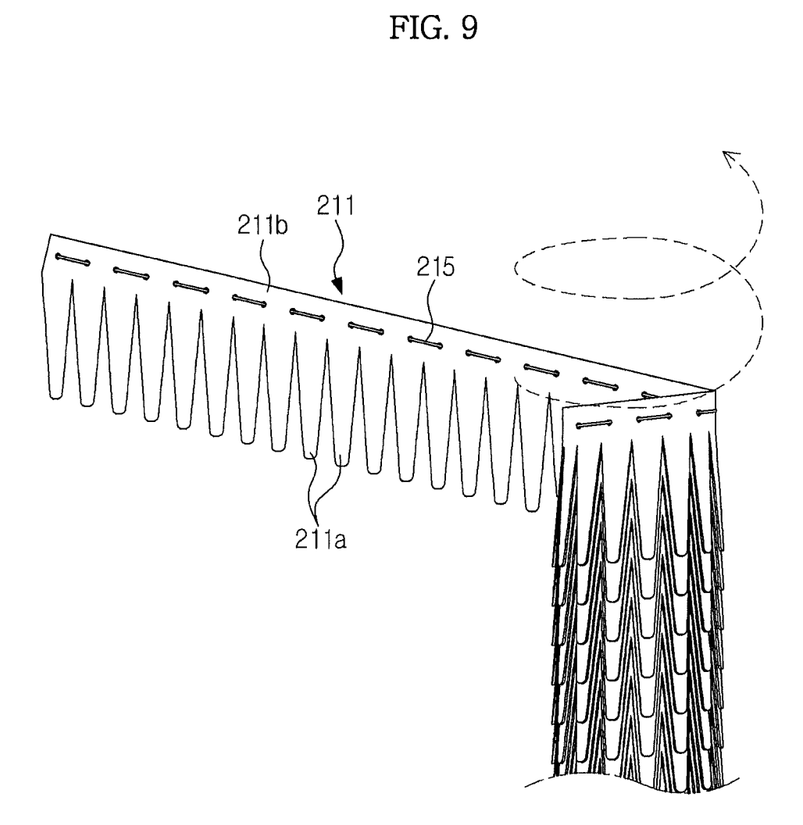
FIG. 9 is an exploded perspective view of a flap member, such as applied in a manipulator, according to one or more embodiments.

Although one or more embodiments have been described with the variably flexible pipe 10 including the link members 122 and the first and second flap members 111,112 disposed on the outer circumferential surfaces of the link members 112, embodiments are not limited thereto. As only an example, FIG. 9 illustrates one or more embodiments where one or more components corresponding to the one or more link members 122 may not be included in the variably flexible pipe. In such one or more embodiments, one flap member 211 may be bent or applied in a longitudinal spiral so as to form a tubular shape, and wires 215 may be employed for support or to cause the flap member 211 to maintain the tubular shape. Here, the aforementioned example tube 14 may also be applied in one or more parts so as to encapsulate both an outer circumference of the one flap member 211 and wires 215 and an inner circumference of the one flap member 211 and wires 215. In one or more embodiments, one or more flap members 211 may be applied in an overlapping manner to form the same tubular shape.

Figure 10:
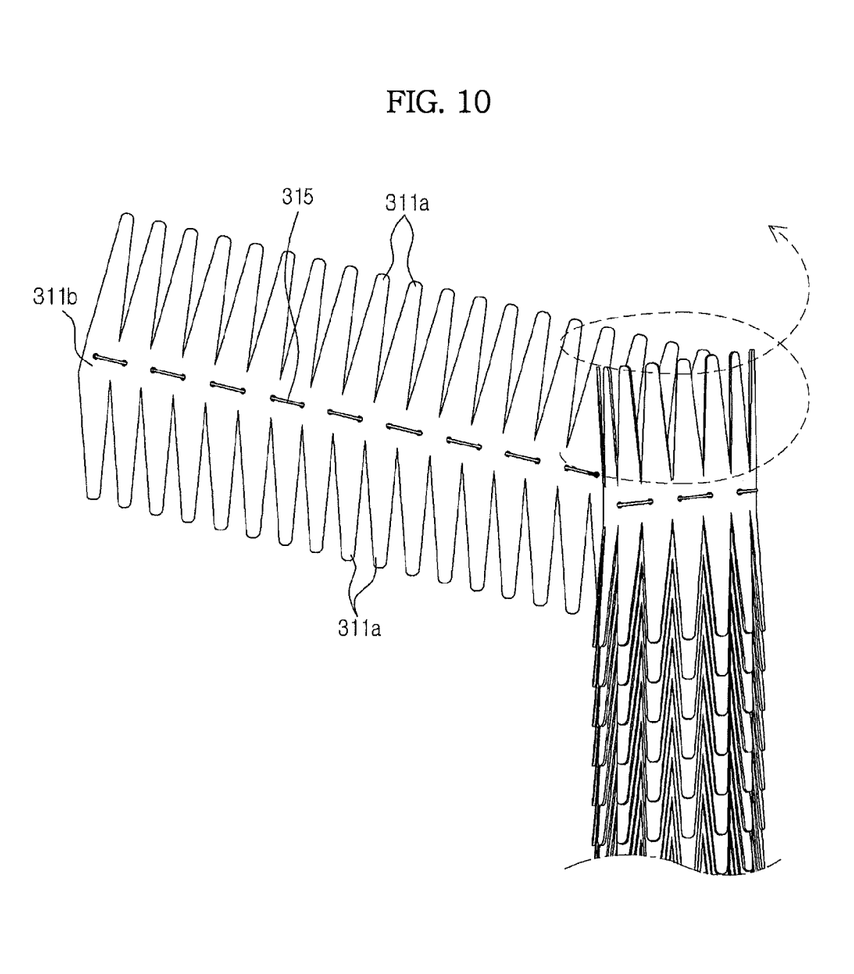
FIG. 10 is an exploded perspective view of a flap member, such as applied in a manipulator, according to one or more embodiments.

Although FIG. 9 illustrates one or more embodiments where flap parts 211a of the flap member 211 extend in one direction, e.g., such as the illustrated downward direction of the flap parts 211a from an upper connection part 211b of the flap member 211, embodiments are not limited thereto. For example, FIG. 10, according to one or more embodiments, illustrates plural flap parts extending in different directions for an example one flap member, where flap parts 311a may extend from a connection part 311b of the one flap member in both illustrated upward and downward directions. In one or more embodiments, such different extended directions of the flap part 311a may configure the variably flexible pipe so that the flap parts 311a are formed toward an inside as well as an outside of the variably flexible pipe.

As is apparent from the above description, a variably flexible pipe in accordance with one or more embodiments may be applied or controlled to change frictional force between components of the variably flexible pipe, e.g., flap parts, by controlling an adjusting of an inner pressure of a tube surrounding the components of the variably flexible pipe, and thus flexibility of the variably flexible pipe is controlled to increase or decrease a capability for flexing of the variably flexible pipe.

While aspects of the present invention have been shown and described with reference to differing embodiments thereof, it should be understood that these embodiments should be considered in a descriptive sense only and not for purposes of limitation. Descriptions of features or aspects within each embodiment should typically be considered as available for other similar features or aspects in the remaining embodiments. Suitable results may equally be achieved if described components are combined in a different manner and/or replaced or supplemented by other components or their equivalents.

Thus, although a few embodiments have been shown and described, with additional embodiments being equally available, it would be appreciated by those skilled in the art that changes may be made in these embodiments without departing from the principles and spirit of the invention, the scope of which is defined in the claims and their equivalents.

What is claimed is:

1. A variably flexible pipe comprising:
    a longitudinal pipe structure including,
        a plurality of link members in respective ring shapes and sequentially positioned in a longitudinal direction such that each of the plurality of link members have an upper surface and a lower surface opposite each other in the longitudinal direction, and an outer surface and an inner surface opposite each other in a direction perpendicular to the longitudinal direction, and a plurality of flap members in respective ring shapes and sequentially positioned in the longitudinal direction, each of the plurality of flap members including a connection part and a plurality of flap parts on the outer surface of respective ones of the plurality of link members, one side of each of the plurality of flap parts being connected to and extending away from the connection part in the longitudinal direction with a width of the plurality of flap parts gradually decreasing in the longitudinal direction such that the plurality of flap members are crown shaped with a hollow interior, the plurality of flap members varying between a first state and a second state;

a tube formed of an elastically deformable material, the tube including an inner surface and an outer surface with both the plurality of link members and the plurality of flap members therebetween such that the inner surface of the tube contacts the plurality of flap members and the outer surface of the tube contacts the plurality of link members, the tube connected to a pneumatic pump controlling a change in a controllable pressure inside the tube to set the plurality of flap members to one of the first state and the second state based on a difference between the controllable pressure inside the tube and a pressure outside of the tube, the second state being a state in which (i) the outer surface of the tube presses against the inner surface of the link members and (ii) the inner surface of the tube presses against the plurality of flap members such that the plurality of flap members provide a compressive force against the outer surface of the link members that is greater than in the second state than the first state; and a plurality of wires configured to pass through the plurality of link members so as to selectively deform the variably flexible longitudinal pipe structure.

2. The variably flexible pipe according to claim 1, wherein each of the plurality of link members includes:

a pair of first hinge parts configured to be at different positions along the upper surface of each of the plurality of link members and connected to a link member neighboring the upper surface; and a pair of second hinge parts configured to be at different positions along the lower surface of each of the plurality of link members and connected to a link member neighboring the lower surface.

3. The variably flexible pipe according to claim 2, wherein the pair of first hinge parts and the pair of second hinge parts are at respectively different positions separated by an angle of 90° in a circumferential direction.

4. The variably flexible pipe according to claim 2, wherein:

the pair of first hinge parts include hinge protrusions configured to protrude in a circular shape and rotatably installed in the pair of second hinge parts; and the pair of second hinge parts include hinge recesses configured to indent in a circular shape so that the hinge protrusions are rotatably installed in the hinge recesses.

5. The variably flexible pipe according to claim 2, wherein the plurality of flap parts cover the pair of first hinge parts and the pair of second hinge parts connecting two neighboring ones of the plurality of link members; and the plurality of flap members includes, a first flap member, the plurality of flap parts of which is extended in a first direction and configured to cover the pair of first hinge parts and the pair of second hinge parts, and a second flap member, the plurality of flap parts of which is extended in a second direction different from the first direction and covers the pair of first hinge parts and the pair of second hinge parts.

6. The variably flexible pipe according to claim 1, wherein:

the plurality of flap members are bent in a spiral shape so as to form a tubular shape; and the tube is configured to cover an outer surface and an inner surface of the plurality of flap members bent in the spiral shape.

7. The variably flexible pipe according to claim 6, wherein the plurality of flap parts are configured to extend from the connection part of the flap member in one direction.

8. The variably flexible pipe according to claim 6, wherein the plurality of flap parts are configured to extend from the connection part in two directions.

9. A manipulator comprising:

a longitudinal pipe structure including, a plurality of link members in respective ring shapes and sequentially positioned in a longitudinal direction such that each of the plurality of link members have an upper surface and a lower surface opposite each other in the longitudinal direction, and an outer surface and an inner surface opposite each other in a direction perpendicular to the longitudinal direction, and a plurality of flap members in respective ring shapes and sequentially positioned in the longitudinal direction, each of the plurality of flap members including a connection part and a plurality of flap parts on the outer surface of respective ones of the plurality of link members, one side of each of the plurality of flap parts being connected to and extending away from the connection part in the longitudinal direction with a width of the plurality of flap parts gradually decreasing in the longitudinal direction such that the plurality of flap members are crown shaped with a hollow interior, the plurality of flap members varying between a first state and a second state;

a tube formed of an elastically deformable material, the tube including an inner surface and an outer surface with both the plurality of link members and the plurality of flap members therebetween such that the inner surface of the tube contacts the plurality of flap members and the outer surface of the tube contacts the plurality of link members, the tube connected to a pneumatic pump controlling a change in a controllable pressure inside the tube to set the plurality of flap members to one of the first state and the second state based on a difference between the controllable pressure inside the tube and a pressure outside of the tube, the second state being a state in which (i) the outer surface of the tube presses against the inner surface of the link members and (ii) the inner surface of the tube presses against the plurality of flap members such that the plurality of flap members provide a compressive force against the outer surface of the link members that is greater than in the second state than the first state;

a plurality of wires configured to pass through the plurality of link members so as to selectively deform the longitudinal pipe structure; and a plurality of actuators respectively configured to apply force to the plurality of wires so as to bend the longitudinal pipe structure.

10. The manipulator according to claim 9, further comprising:
the pneumatic pump configured to control the change in the controllable pressure inside the tube and control the longitudinal pipe structure to be in one of the first state and second state.

11. The manipulator according to claim 9, wherein each of the plurality of link members includes:
a pair of first hinge parts configured to be at different positions along the upper surface of each of the plurality of link members and connected to a link member neighboring the upper surface; and
a pair of second hinge parts configured to be at different positions along the lower surface of each of the plurality of link members and connected to another link member neighboring the lower surface.

12. The manipulator according to claim 11, wherein the pair of first hinge parts and the pair of second hinge parts are at respectively different positions separated by an angle of 90° in a circumferential direction.

13. The manipulator according to claim 11, wherein:
the first hinge parts include hinge protrusions configured to protrude in a circular shape and rotatably installed in the second hinge parts; and
the second hinge parts include hinge recesses configured to be indented in a circular shape so that the hinge protrusions are rotatably installed in the hinge recesses.

14. The manipulator according to claim 11, wherein:
the plurality of flap parts cover the pair of first hinge parts and the pair of second hinge parts connecting two neighboring ones of the plurality of link members; and
the plurality of flap members includes,
a first flap member, the plurality of flap parts of which is extended in a first direction and configured to cover the pair of first hinge parts and the pair of second hinge parts, and
a second flap member, the plurality of flap parts of which is extended in a second direction different from the first direction and configured to cover the pair of first hinge parts and the pair of second hinge parts.

15. The manipulator according to claim 9, wherein:
the plurality of flap members are configured to bend in a spiral shape so as to form a tubular shape; and
the tube is configured to cover an outer surface and an inner surface of the plurality of flap members bent in the spiral shape.

16. The manipulator according to claim 15, wherein the plurality of flap parts are configured to extend from the connection part in one direction.

17. The manipulator according to claim 15, wherein the plurality of flap parts are configured to extend from the connection part in two directions.

* * * * *